United States Patent
Shanmuganandamurthy et al.

(10) Patent No.: US 7,488,830 B2
(45) Date of Patent: Feb. 10, 2009

(54) IMIDAZOLIDINE-2,4-DIONE MONOMERS, USEFUL IN MAKING HYDANTOIN POLYMERS

(75) Inventors: Krishnamurthy Shanmuganandamurthy, Plainsboro, NJ (US); Euen Gunn, Trenton, NJ (US); Stewart Alexander Warburton, West Windsor, NJ (US)

(73) Assignee: Rhodia Inc., Cranbury, NJ (US)

( * ) Notice: Subject to any disclaimer, the term of this patent is extended or adjusted under 35 U.S.C. 154(b) by 112 days.

(21) Appl. No.: 11/493,334

(22) Filed: Jul. 26, 2006

(65) Prior Publication Data

US 2007/0025946 A1 Feb. 1, 2007

(51) Int. Cl.
C07D 233/02 (2006.01)
(52) U.S. Cl. .............. 548/317.5; 548/319.5; 548/320.5; 548/324.5
(58) Field of Classification Search ............... 548/320, 548/317.5, 319.5, 324.5
See application file for complete search history.

(56) References Cited

U.S. PATENT DOCUMENTS

| | | | | |
|---|---|---|---|---|
| 4,319,032 A | * | 3/1982 | Sandri et al. ............ 548/323.5 |
| 5,194,260 A | | 3/1993 | Grollier et al. ............ 424/72 |
| 6,416,770 B1 | | 7/2002 | Leduc et al. ............ 424/401 |
| 6,515,138 B2 | | 2/2003 | Weir et al. ............ 548/324 |

\* cited by examiner

Primary Examiner—Kamal A Saeed
Assistant Examiner—Yong Chu

(57) ABSTRACT

A polymer that includes at least one monomeric unit having a pendant substituent group according to formula (II):

(II)

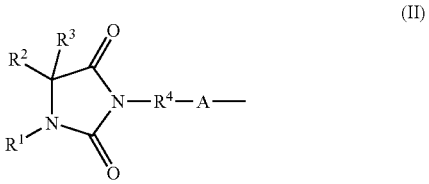

wherein:
$R^1$ is H, chloro, bromo, alkyl, hydroxyalkyl, aryl, or aralkyl,
$R^2$ and $R^3$ are each independently H, alkyl, hydroxyalkyl, aryl, aralkyl, uriedo, or carboxyalkylene,
$R^4$ is alkylene or

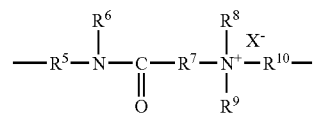

$R^5$, $R^7$, and $R^{10}$ are each independently alkylene,
$R^6$, $R^8$, and $R^9$ are each independently H or alkyl,
A is O or N—$R^{11}$, provided if A is O and $R^4$ is methylene, then $R^1$ cannot be H, chloro, or bromo,
$R^{11}$ is H or alkyl, and
$X^-$ is an anion,
is useful in personal care application, such as hair styling compositions.

13 Claims, No Drawings

IMIDAZOLIDINE-2,4-DIONE MONOMERS, USEFUL IN MAKING HYDANTOIN POLYMERS

FIELD OF THE INVENTION

This invention relates to polymers having heterocyclic substituent groups, to monomers useful in making such polymers, and to compositions containing such polymers.

BACKGROUND OF THE INVENTION

Many shampoos and hair care products contain conditioning agents, which are typically high molecular weight polymers and which may be either synthetic or derived from natural sources. One benefit provided by conditioning agents is a reduction in the amount of work necessary to comb through the conditioned hair. Polymeric conditioning agents may also function as adjuvants in the delivery of supplemental conditioning agents, such as silicones.

There is a continuing interest in the art in developing hair conditioning agents that provide high conditioning performance at low concentrations.

SUMMARY OF THE INVENTION

In a first aspect, the present invention is directed to a monomer according to formula (I):

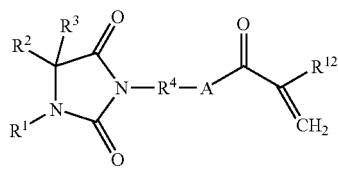

wherein:
$R^1$ is H, chloro, bromo, alkyl, hydroxyalkyl, aryl, or aralkyl,
$R^2$ and $R^3$ are each independently H, alkyl, hydroxyalkyl, aryl, aralkyl, uriedo, or carboxyalkylene,
$R^4$ is alkylene or

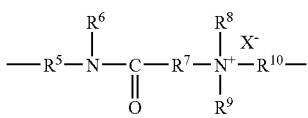

$R^5$, $R^7$, and $R^{10}$ are each independently alkylene,
$R^6$, $R^8$, and $R^9$ are each independently H or alkyl,
A is O or N—$R^{11}$, provided if A is O and $R^4$ is methylene, then $R^1$ cannot be H, chloro, or bromo,
$R^{11}$ is H or alkyl,
$R^{12}$ is H or ($C_1$-$C_6$)alkyl, and
$X^-$ is an anion.

In a second aspect, the present invention is directed to a polymer comprising at least one monomeric unit having a pendant substituent group according to formula (II):

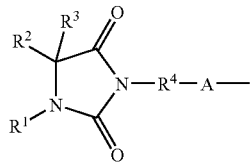

wherein:
$R^1$ is H, chloro, bromo, alkyl, hydroxyalkyl, aryl, or aralkyl,
$R^2$ and $R^3$ are each independently H, alkyl, hydroxyalkyl, aryl, aralkyl, uriedo, or carboxyalkylene,
$R^4$ is alkylene or

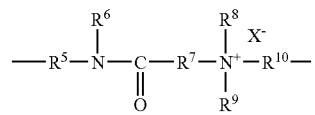

$R^5$, $R^7$, and $R^{10}$ are each independently alkylene,
$R^6$, $R^8$, and $R^9$ are each independently H or alkyl,
A is O or N—$R^{11}$, provided if A is O and $R^4$ is methylene, then $R^1$ cannot be H, chloro, or bromo,
$R^{11}$ is H or alkyl, and
$X^-$ is an anion.

In a third aspect, the present invention is directed to a personal care composition, comprising:

(a) a hydantoin-functional polymer comprising at least one monomeric unit having a pendant substituent group according to formula (II):

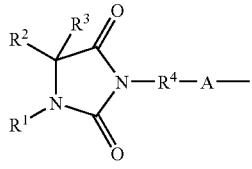

wherein:
$R^1$ is H, chloro, bromo, alkyl, hydroxyalkyl, aryl, or aralkyl,
$R^2$ and $R^3$ are each independently H, alkyl, hydroxyalkyl, aryl, aralkyl, uriedo, or carboxyalkylene,
$R^4$ is alkylene or

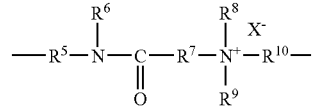

$R^5$, $R^7$, and $R^{10}$ are each independently alkylene,
$R^6$, $R^8$, and $R^9$ are each independently H or alkyl,
A is O or N—$R^{11}$,
$R^{11}$ is H or alkyl, and
$X^-$ is an anion, and (b) a carrier.

DETAILED DESCRIPTION OF INVENTION AND PREFERRED EMBODIMENTS

As used herein, the term "alkyl" means a saturated hydrocarbon radical, more typically a saturated ($C_1$-$C_{18}$) hydrocarbon radical, which may be straight, branched, or cyclic, such as, for example, methyl, ethyl, n-propyl, iso-propyl, n-butyl, sec-butyl, t-butyl, pentyl, n-hexyl, cyclohexyl.

As used herein, the term "hydroxyalkyl" means an alkyl radical, more typically a ($C_1$-$C_{18}$) alkyl radical, that is substituted with one or more hydroxyl groups, such as, for example, hydroxyethyl, hydroxypropyl.

As used herein, the term "alkylene" means a bivalent acyclic saturated hydrocarbon radical, more typically a bivalent acyclic saturated ($C_1$-$C_{18}$) hydrocarbon radical, such as, for example, methylene, polymethylene, and alkyl substituted polymethylene radicals, such as, for example, dimethylene, tetramethylene, 2-methyltrimethylene.

As used herein, the term "alkenyl" means an unsaturated hydrocarbon radical, more typically an unsaturated ($C_1$-$C_{18}$) hydrocarbon radical, that may be straight, branched, or cyclic and that contains one or more carbon-carbon double bonds, such as, for example, ethenyl, 1-propenyl, 2-propenyl, cyclopentenyl.

As used herein, the term "aryl" means an unsaturated hydrocarbon radical that contains one or more six-membered carbon rings, more typically a single six-membered carbon ring, in which the unsaturation may be represented by three conjugated carbon-carbon double bonds, which may be substituted one or more of the ring carbons with hydrocarbon, typically alkyl or alkenyl, halo, or haloalkyl groups, such as, for example, phenyl, methylphenyl, trimethylphenyl, chlorophenyl, trichloromethylphenyl.

As used herein, the term "aralkyl" means an alkyl group, more typically ($C_1$-$C_{18}$)alkyl group, that is substituted with one or more aryl groups, such as, for example, phenylmethyl, phenylethyl, triphenylmethyl.

As used herein, the term "halo" means chloro, bromo, iodo, or fluoro.

As sued herein, the term "haloalkyl means an alkyl radical, more typically a ($C_1$-$C_{18}$) alkyl radical, that is substituted on one or more carbon atoms with one or more halo groups, such as, for example, chloromethyl, trichloromethyl.

As used herein, the terminology "ethylenic unsaturation" means a terminal (that is, α, β) carbon-carbon double bond.

As used herein, the terminology "($C_n$-$C_m$)" in reference to an organic group, wherein n and m are each integers, indicates that the group may contain from n carbon atoms to m carbon atoms per group.

As used herein, the term "anion" means an organic or inorganic ion, such as, for example, chloride, bromide, acetate, maleate, citrate, more typically, chloride or bromide.

In one embodiment, the polymer according to the present invention comprises at least one monomeric unit, more typically two or more monomeric units, according to formula (III):

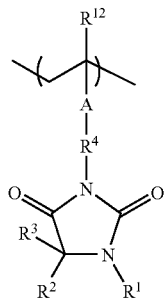

wherein $R^1$ is H, chloro, bromo, alkyl, hydroxyalkyl, aryl, or aralkyl, $R^2$ and $R^3$ are each independently H, alkyl, hydroxyalkyl, aryl, aralkyl, uriedo, or carboxyalkylene, $R^4$ is alkylene or

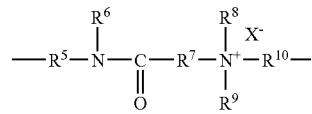

$R^5$, $R^7$, and $R^{10}$ are each independently alkylene, $R^6$, $R^8$, and $R^9$ are each independently H or alkyl, A is O or N—$R^{11}$, provided that if A is O and $R^4$ is methylene, then, except in the case of the hydantoin-functional polymer component of the personal care composition of the present invention, $R^1$ cannot be H, chloro, or bromo, $R^{11}$ is H or alkyl, $R^{12}$ is H or ($C_1$-$C_6$)alkyl, and $X^-$ is an anion.

In one embodiment of the monomer according to formula (I), in one embodiment of the polymer comprising at least one monomeric unit having a pendant substituent group according to formula (II), and in one embodiment of the polymer comprising at least one monomeric unit according to formula (III):

$R^1$ is H, ($C_1$-$C_{12}$)alkyl, hydroxy($C_1$-$C_{12}$)alkyl, phenyl, or benzyl, $R^2$ and $R^3$ are each independently H, ($C_1$-$C_{12}$)alkyl, hydroxy($C_1$-$C_{12}$)alkyl, phenyl, benzyl, uriedo, or carboxy ($C_1$-$C_{12}$)alkylene, $R^4$ is ($C_1$-$C_{12}$)alkylene or

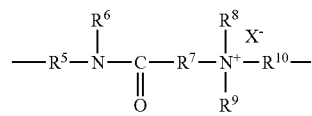

$R^5$, $R^7$, and $R^{10}$ are each independently ($C_1$-$C_{12}$)alkylene, $R^6$, $R^8$, and $R^9$ are each independently H or ($C_1$-$C_{12}$)alkyl, A is O or N—$R^{11}$, provided that if A is O and A is methylene, then, except in the case of the hydantoin-functional polymer component of the personal care composition of the present invention, $R^1$ cannot be H, $R^{11}$ is H or ($C_1$-$C_{12}$)alkyl, and $X^-$ is an anion, more typically chloride or bromide, and, in the case of the monomer and of the polymer comprising at least one monomeric unit according to formula (III), $R^{12}$ is H or $(C_1-C_6)$alkyl, more typically H or methyl.

In one embodiment of the monomer according to formula (I), in one embodiment of the polymer comprising at least one monomeric unit having a pendant substituent group according to formula (II), and in one embodiment of the polymer comprising at least one monomeric unit according to formula (III):

$R^1$ is H, or $(C_1-C_6)$alkyl, phenyl or benzyl, more typically H, methyl, or ethyl, $R^2$ and $R^3$ are each independently H, or $(C_1-C_6)$alkyl, phenyl or benzyl, more typically H, methyl, or ethyl, $R^4$ is $(C_1-C_6)$alkylene, more typically, methylene, dimethylene, or trimethylene, A is $N-R^{11}$, and $R^{11}$ is H or $(C_1-C_6)$alkyl, more typically H, methyl, or ethyl, and, in the case of the monomer and of the polymer comprising at least one monomeric unit according to formula (III), $R^{12}$ is H or $(C_1-C_6)$alkyl, more typically H or methyl.

In one embodiment of the monomer according to formula (I), in one embodiment of the polymer comprising at least one monomeric unit having a pendant substituent group according to formula (II), and in one embodiment of the polymer comprising at least one monomeric unit according to formula (III):

$R^1$ is H, or $(C_1-C_6)$alkyl, phenyl or benzyl, more typically H, methyl, or ethyl, $R^2$ and $R^3$ are each independently H, or $(C_1-C_6)$alkyl, phenyl or benzyl, more typically H, methyl, or ethyl, $R^4$ is

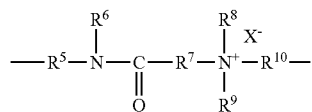

$R^5$, $R^7$, and $R^{10}$ are each independently $(C_1-C_6)$alkylene, more typically methylene dimethylene, or trimethylene, $R^6$, $R^8$, and $R^9$ are each independently H or $(C_1-C_6)$alkyl, more typically H, methyl or ethyl, A is $N-R^{11}$, $R^{11}$ is H or $(C_1-C_6)$alkyl, more typically H, methyl or ethyl, and $X^-$ is an anion, more typically chloride or bromide, and, in the case of the monomer and of the polymer comprising at least one monomeric unit according to formula (III), $R^{12}$ is H or $(C_1-C_6)$alkyl, more typically H or methyl.

The monomer according to the present invention can be made by known synthesis techniques from commercially available starting material.

In one embodiment, the polymer of the present invention or the hydantoin-functional polymer component of the personal care composition of the present invention is made by free radical polymerization of one or more ethylenically unsaturated monomers comprising at least one monomer that comprises at least one site of ethylenic unsaturation per molecule and at least one moiety according to formula (II), wherein $R^1$ to $R^{11}$, A, and $X^-$ are each as described above, per molecule of monomer, such as, for example, monomers according to formula (I), wherein $R^1$ to $R^{12}$, A, and $X^-$ are each as described above. As used herein, the notation "$R^x$ to $R^{(x+y)}$", wherein x and y are each positive integers, means from substituent group $R^x$ to substituent group $R^{(x+y)}$, inclusive of any substituent groups between substituent group $R^x$ and substituent group $R^{(x+y)}$, for example, "$R^1$ to $R^{12}$" means $R^1$, $R^2$, $R^3$, $R^4$ $R^5$, $R^6$, $R^7$, $R^8$, $R^9$, $R^{10}$ $R^{11}$ and $R^{12}$. As used herein, an indication certain substituent group of an embodiment of the invention is "as described above" refers separately to each previous description, including the broadest description and any narrower descriptions, of such substituent group that is applicable in the context of that embodiment.

in an alternative embodiment, the polymer of the present invention or the hydantoin-functional polymer component of the personal care composition of the present invention is made by grafting at least one moiety according to formula (II), wherein $R^1$ to $R^{11}$, A, and $X^-$ are each as described above, to a polymer backbone, such as, for example, a poly(acrylonitrile) polymer backbone, according to known techniques.

In one embodiment, the polymer of the present invention or the polymer component of the personal care composition of the present invention consists essentially of two or more monomeric units each independently derived from a monomer that comprises at least one site of ethylenic unsaturation per molecule and at least one moiety according to formula (II), wherein $R^1$ to $R^{11}$, A, and $X^-$ are each as described above, per molecule of monomer.

In one embodiment, the polymer of the present invention or the hydantoin-functional polymer component of the personal care composition of the present invention is a homopolymer that consists essentially of two or more identical monomeric units each derived from a monomer comprising at least one site of ethylenic unsaturation per molecule and at least one moiety according to formula (II), wherein $R^1$ to $R^{11}$, A, and $X^-$ are each as described above, per molecule, more typically, from a monomer according to formula (I), wherein $R^1$ to $R^{12}$, A, and $X^-$ are each as described above.

In one embodiment, the polymer of the present invention or the hydantoin-functional polymer component of the personal care composition of the present invention is a homopolymer consisting essentially of two or more identical monomeric units according to formula (III), wherein $R^1$ to $R^{12}$, A, and $X^-$ are each as described above.

In one embodiment, the polymer of the present invention or the hydantoin-functional polymer component of the personal care composition of the present invention is a copolymer comprising a two or more monomeric units, wherein at least one of such monomeric units comprises a pendant substituent group according to formula (II), wherein $R^1$ to $R^{11}$, A, and $X^-$ are each as described above, and at least one other of such monomeric units lacks such a substituent group In one embodiment, the polymer of the present invention or the hydantoin-functional polymer component of the personal care composition of the present invention is a copolymer comprising at least one first monomeric unit derived from a monomer that comprises at least one site of ethylenic unsaturation per molecule and at least one moiety according to formula (II), wherein $R^1$ to $R^{11}$, A, and $X^-$ are each as described above, per molecule, more typically, from a monomer according to formula (I), wherein $R^1$ to $R^{12}$, A, and $X^-$ are each as described above, and at least one second monomeric unit derived from another ethylenically unsaturated monomer that is copolymerizable with the monomer from which the first monomeric unit is derived.

In one embodiment, the polymer of the present invention or the hydantoin-functional polymer component of the personal care composition of the present invention is a copolymer comprising at least one monomeric unit according to formula (III), wherein $R^1$ to $R^{12}$, A, and $X^-$ are each as described above, and at least one second monomeric unit derived from another ethylenically saturated monomer that is copolymerizable with the monomer from which the first monomeric unit is derived.

In one embodiment, the polymer of the present invention or the hydantoin-functional polymer component of the personal care composition of the present invention is a copolymer comprising at least one monomeric unit derived from a monomer according to formula (II), wherein $R^1$ to $R^{11}$, A, and $X^-$ are each as described above, and at least one monomeric unit derived from another ethylenically saturated monomer that is copolymerizable with the monomer according to formula (II).

Suitable ethylenically unsaturated comonomers are known compounds and include, for example, esters of ethylenically unsaturated carboxylic acids, such as ethyl acrylate, methyl methacrylate, n-propyl acrylate, n-propyl methacrylate, n-butyl acrylate, n-butyl methacrylate, 2-ethylhexyl acrylate, 2-ethylhexyl methacrylate, hydroxyethyl acrylate, hydroxyethyl methacrylate, hydroxypropylacrylate, hydroxypropylmethacrylate, cyclohexyl acrylate, cyclohexyl methacrylate, N,N-dimethylaminoethyl acrylate methyl chloride, N,N-dimethylaminoethyl methacrylate methyl chloride, benzyldimethylammonium ethyl acrylate chloride, and benzyldimethylammonium ethyl methacrylate chloride, amides of ethylenically unsaturated carboxylic acids, such as acrylamide, methacrylamide, trimethylammonium propyl acrylamide chloride, and trimethylammonium propyl methacrylamide chloride, vinyl monomers, such as vinyl acetate, vinyl pyrrolidone, vinyl caprolactam, and vinyl versatate, and allylic monomers, such as allyl alcohol.

In one embodiment, the polymer of the present invention or the hydantoin-functional polymer component of the personal care composition of the present invention is a copolymer comprising at least one first monomeric unit according to formula (III) and at least one second monomeric unit according to formula (IV):

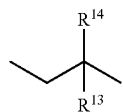
(IV)

wherein:

$R^{13}$ is hydroxyalkyl,

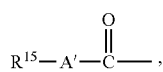

or

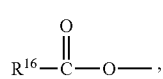

$R^{14}$ is H or $(C_1$-$C_4)$alkyl,

A' is O or $NR^{17}$, $R^{15}$ and $R^{16}$ are each independently alkyl or hydroxyalkyl, and $R^{17}$ is H or alkyl.

In one embodiment, the polymer of the present invention or the hydantoin-functional polymer component of the personal care composition of the present invention is a copolymer that comprises:

(a) from about 0.5 to about 99.5 mole percent first monomeric units, each of which:
  (i) is derived from a monomer according to formula (I), wherein $R^1$ to $R^{12}$, A, and $X^-$ are each as described above,
  (ii) comprises a pendant substituent group according to formula (II), wherein $R^1$ to $R^{11}$, A, and $X^-$ are each as described above, and/or
  (iii) is according to formula (III), wherein $R^1$ to $R^{12}$, A, and $X^-$ are each as described above, and
(b) from about 0.5 to about 99.5 mole percent second monomeric units, each of which:
  (i) lacks a pendant substituent group according to formula (II), and/or
  (ii) is derived from a monomer according to formula (IV), wherein $R^{13}$ to $R^{17}$ and A' are each as described above.

In one embodiment, the polymer of the present invention or the hydantoin-functional polymer component of the personal care composition of the present invention is a copolymer that comprises:

(a) from about 0.5 to less than 50 mole percent first monomeric units, each of which:
  (i) is derived from a monomer according to formula (I), wherein $R^1$ to $R^{12}$, A, and $X^-$ are each as described above,
  (ii) comprises a pendant substituent group according to formula (II), wherein $R^1$ to $R^{11}$, A, and $X^-$ are each as described above, and/or
  (iii) is according to formula (III), wherein $R^1$ to $R^{12}$, A, and $X^-$ are each as described above, and
(b) from 50 to about 99.5 mole percent second monomeric units, each of which:
  (i) lacks a pendant substituent group according to formula (II), and/or
  (ii) is derived from a monomer according to formula (IV), wherein $R^{13}$ to $R^{17}$ and A' are each as described above.

In one embodiment, the polymer of the present invention or the hydantoin-functional polymer component of the personal care composition of the present invention is a copolymer that comprises:

(a) from 50 to about 99.5 mole percent first monomeric units, each of which:
  (i) is derived from a monomer according to formula (I), wherein $R^1$ to $R^{12}$, A, and $X^-$ are each as described above,
  (ii) comprises a pendant substituent group according to formula (II), wherein $R^1$ to $R^{11}$, A, and $X^-$ are each as described above, and/or
  (iii) is according to formula (III), wherein $R^1$ to $R^{12}$, A, and $X^-$ are each as described above, and
(b) from about 0.5 to less than 50 mole percent second monomeric units, each of which:
  (i) lacks a pendant substituent group according to formula (II), and/or
  (ii) is derived from a monomer according to formula (IV), wherein $R^{13}$ to $R^{17}$ and A' are each as described above.

In one embodiment, the polymer of the present invention or the hydantoin-functional polymer component of the personal care composition of the present invention exhibits a weight average molecular weight of from about 1,000 to about 5,000,000 grams per mole ("g/mol"), more typically from about 5,000 to about 4,000,000 g/mol, even more typically from about 10,000 to about 2,000,000 g/mol. The weight average molecular weight of a polymer is typically determined by fractionating a solution of the polymer using, for example, size exclusion chromatography, and then determining the molecular weight of each of such polymer fractions, for example, by measuring the intensity of light scattering by the fractions or by measuring the refractive index of the fractions and comparing the refractive index results to those obtained for a polymer of known molecular weight.

In one embodiment, the polymer of the present invention or the hydantoin-functional polymer component of the personal care composition of the present invention is at least substantially, that is, at least 0.5% polymer by weight at 20° C., soluble in water, in a $(C_1-C_6)$alkanol, or in a mixture of water and a $(C_1-C_6)$alkanol.

As used herein, the terminology "personal care compositions" means compositions for use in caring for the hair or skin, and includes, for example, shampoos, hair conditioners, hair gels, hair mousses, hair sprays, skin cleansers, and skin lotions.

Personal care compositions according to the present invention may, optionally, further comprise one or more surfactant compounds. Surfactant compounds are characterized by the presence of both a hydrophilic group and a hydrophobic group on the same molecule and include amphoteric surfactants, Zwitterionic surfactants, nonionic surfactants, anionic surfactants, cationic surfactants or combinations thereof.

Anionic surfactants are ionic surfactant compounds that have a negative electrical charge associated with the hydrophilic portion of the surfactant. Suitable anionic surfactants include, generally, alkyl sulfonates, aryl sulfonates, alkaryl sulfonates, alpha olefin sulfonates, paraffin sulfonates, alkyl ester sulfonates, alkyl sulfates, alkyl alkoxy sulfates, alkyl alkoxy carboxylates, alkyl alkoxylated sulfates, acylsarcosinates, and amidosulfonates, as well as mixtures thereof.

Cationic surfactants are ionic surfactant compounds that have a positive electrical charge associated with the hydrophilic portion of the surfactant. Suitable cationic surfactants are generally compounds according to formula (V) below:

(V)

wherein $R^{21}$, $R^{22}$, $R^{23}$, and $R^{24}$, are each independently hydrogen, or an organic radical, provided that at least one of $R^{21}$, $R^{22}$, $R^{23}$, and $R^{24}$ is an organic radical, and $X'^-$ is an anion, and include amine salts, such as ethoxylated tallow amine, quaternary ammonium compounds, cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium, chloridedistearyldimonium chloride, isostearyl benzylimidonium chloride, and mixtures thereof.

Amphoteric surfactants are ionic surfactant compounds that are characterized by the presence of two ionic sites on the same molecule and which, depending on the pH of the surrounding medium, may carry a negative electrical charge, a positive electrical charge, or both a negative electrical charge and a positive electrical charge on the same molecule. Suitable amphoteric surfactants include alkali metal, alkaline earth metal, ammonium, or substituted ammonium salts of alkyl amphocarboxy glycinates and alkyl amphocarboxypropionates, alkyl amphodipropionates, alkyl amphodiacetates, alkyl amphoglycinates alkyl amphopropionates, alkyl iminopropionates, alkyl iminodipropionates and alkyl amphopropylsulfonates, such as for example, cocoamphoacetate cocoamphopropionate, lauroamphodiacetate, and cocoamphopropyl sulfonate.

Zwitterionic surfactants are ionic surfactant compounds characterized by the presence of two ionic sites per molecule, wherein one of the ionic sites carries a positive electrical charge regardless of the pH of the surrounding medium and wherein the other ionic site may, depending on the pH of the surrounding medium, carry a positive charge. Suitable Zwitterionic surfactants include alkyl betaines, such as cocodimethyl carboxymethyl betaine, amidopropyl betaines, and alkyl sultaines, such as cocodimethyl sulfopropyl betaine, stearyldimethyl sulfopropyl betaine, and alkylamidopropylhydroxy sultaines.

Nonionic surfactants are surfactant compounds that do not dissociate into ions and that not have an electrical charge associated with them. Suitable nonionic surfactants include alkanolamides such as cocamide DEA, lauramide MEA, alkyl amine oxides such as lauramine oxide, polysorbates and ethoxylated sorbitan esters such as sorbitan laurate, PEG-80 sorbitan, and polysorbate-80, fatty acids and fatty acid esters, such as isostearic acid, fatty alcohols and ethoxylated fatty alcohols, such as lauryl alcohol, laureth-4, trideceth alcohol, and C11-15 pareth-9.

In one embodiment, the personal care composition according to the present invention comprises, based on 100 parts by weight ("pbw") of the composition, from about 0.01 to about 80 pbw of the hydantoin-functional polymer component and from about 20 to about 99.9 pbw of a carrier.

Suitable carriers for the personal care composition of the present invention are liquid or solid vehicles that is capable of being mixed with the hydantoin-functional polymer for delivery of the polymer to the hair or skin and that will not cause harm when topically applied to the hair or skin. Suitable liquid carriers include water, organic solvents, such as alkanols, acetone, and isoparrafins, and alkylether diols, mixtures of such organic solvents, and mixtures of water with water miscible organic solvents. Suitable alkanols are typically $(C_1-C_{18})$alkanols and include monohydric alkanols, such as methanol, ethanol, isopropanol, Cetyl Alcohol, Stearyl Alcohol, Cetearyl Alcohol, Benzyl Alcohol, Oleyl Alcohol, and polyhydric alkanols, such as 2-butoxyethanol, and ethylene glycol, as well as mixtures of such alkanols. Suitable alkylether diols include, for example, ethylene glycol monoethyl ether, propylene glycol monoethyl ether and diethylene glycol monomethyl ether, and mixtures thereof.

In one embodiment, the personal care composition according the present invention is an aqueous system wherein the carrier comprises water.

In one embodiment, the personal care composition of the present invention comprises, based on 100 pbw solids (that is absent water and other solvents) of such composition, up to about 6 pbw amphoteric surfactants, up to about 8 pbw Zwitterionic surfactants, up to about 20 pbw anionic surfactants, wherein the total amount of all surfactants ranges from about 6 pbw to about 25 pbw, more typically from about 10 pbw to about 20 pbw.

The personal care compositions according to the present invention may, optionally, further contain other ingredients, such as, for example, preservatives such as benzyl alcohol, methyl paraben, propyl paraben and imidazolidinyl urea, thickeners and viscosity modifiers such as block polymers of ethylene oxide and propylene oxide, electrolytes, such as sodium chloride, sodium sulfate, polyvinyl alcohol, and ethyl alcohol, pH adjusting agents such as citric acid, succinic acid, phosphoric acid, sodium hydroxide, sodium carbonate, perfumes, dyes, conditioning agents such as organosilicon materials, including, silicone gums, polyorganosiloxane fluids, and silicone resins, active ingredients such as anti-dandruff agents (zinc pyrithion), vitamins or their derivatives such as Vitamin B, Vitamin E Acetate, and sequestering agents such as disodium ethylene diamine tetra-acetate.

In one embodiment, the personal care composition of the present invention comprises, based on 100 pbw of the personal care composition and independently for each such ingredient, up to about 10 pbw, preferably from 0.5 pbw to about 5.0 pbw, of such other ingredients, depending on the desired properties of the hair care composition.

In one embodiment, the personal care composition is a hair styling composition that is in the form of a gel, mousse, or spray and may be applied to the hair and/or skin, for example, by hand or by spraying, as appropriate in view of the form of the composition.

In one embodiment, the personal care composition is a hair styling gel that comprises a hydantoin-functional polymer component, a carrier selected from water, $(C_2-C_6)$alkanols, and mixtures thereof, and, optionally, a thickener. Suitable thickeners include acrylic acid polymers and copolymers, such as a Carbomers.

As used herein, the term "mousse" means a composition that is in the form of a foam when applied. In one embodiment, the personal care composition is a hair styling mousse is packaged in a pressurized container and comprises a hydantoin-functional polymer component, a carrier, and a propellant suitable for foaming the composition when the composition is dispensed from the container. Suitable propellants are liquefiable gases, such as, for example, propane, butane, isobutane, nitrogen, carbon dioxide, nitrous oxide, 1,2-difluoroethane.

In one embodiment, the personal care composition is a hair spray composition suitable for spray application from a container that is equipped with a mechanical sprayer, comprising a hydantoin-functional polymer component, and a carrier selected from water, $(C_2-C_6)$alkanols, and mixtures thereof.

In one embodiment, the personal care composition is an aerosol hair spray composition suitable for spray application from a pressurized container and comprises, a hydantoin-functional polymer component, a carrier, typically a $(C_1-C_6)$ alkanol or $(C_7-C_{10})$ isoparrafin carrier, and a propellant suitable for aerosol delivery of the hair spray composition to the hair. Suitable propellants are those described above in regard to the hair styling mousse embodiment of the personal care composition of the present invention.

The personal care composition of the present invention is used by applying the personal composition to the hair and/or skin.

The polymer of the present invention is also useful as a component in fabric care compositions and home care compositions. As used herein, the terminology "fabric care compositions" means compositions for use in caring for fabrics such as clothing and includes, for example, laundry detergents.

In one embodiment, the present invention is directed to a fabric care composition that comprises at least one polymer according to the present invention, one or more surfactant compounds, and, optionally, further comprising a textile compatible carrier such as for example, water.

The fabric care composition may optionally further comprise other components know or appropriate for use in such compositions, such as, for example, softening agents, such a lanolin, non-aqueous solvents, perfume carriers, fluorescers, colorants, hydrotropes, antifoaming agents, antiredeposition agents, enzymes, optical brightening agents, opacifiers, anti-shrinking agents, anti-wrinkle agents, anti-spotting agents, dye transfer inhibitors, germicides, fungicides, anti-oxidants, UV absorbers (sunscreens), heavy metal sequestrants, chlorine scavengers, dye fixatives, anti-corrosion agents, drape imparting agents, antistatic agents and ironing aids.

Suitable fabric care compositions include pretreatment products, soaking products, main wash products, and rinse treatments, may be in the form of a liquid, solid, a gel or paste, spray, stick, or mousse, and may be applied to a substrate such as a flexible sheet or via a dispenser for use in a wash cycle, rinse cycle, or dryer cycle.

Example 1

A monomer according to the formula:

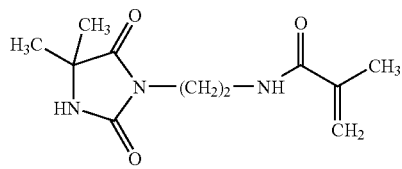

is made as described below.

3-(2-propionamidoethyl)-5,5'-dimethyl hydantoin is made as follows. A mixture of 128 grams ("g") (1 mole) of 5,5'-dimethylhydantoin and 99 g (1 mole) of 2-ethyl oxazoline is placed in a 1 liter ("L") round-bottom flask equipped with a condenser. The mixture is heated with stirring to 130° C. and maintained at this temperature for 6.5 hours. The product is isolated by recrystallization from a mixture of ethylacetate and methanol (60/40 weight ratio).

3-(2-monohydrochloride aminoethyl)-5,5'-dimethyl hydantoin is made as follows. A mixture of 110 g (0.485 mole) of 3-(2-propionamidoethyl)-5,5'-dimethyl hydantoin, 81.0 milliliters ("m") of concentrated HCl and 250 mL of water is placed in a 1 L round-bottom flask equipped with a condenser. The contents of the flask are heated with stirring to reflux temperature, and maintained at reflux for 12 hours. The contents are then concentrated using rotavap under reduced pressure to remove the propionic acid. The resulting concentrate is added to 100 mL of methanol. The white crystals formed are filtered and dried.

3-(2-aminoethyl)-5,5-dimethyl hydantoin is made as follows. A mixture of 61.7 g (0.297 mole) of 3-(2-monohydrochloride aminoethyl)-5,5'-dimethyl hydantoin, 24.8 g (25% solution, 0.3 mole) of NaOH, and 52 g of water are stirred at room temperature for 10 minutes. The water is removed using a rotavap under reduced pressure. The resulting free amine is dissolved in methanol (200 mL) to precipitate NaCl. The methanol is then removed under reduced pressure.

A mixture of 17.1 g (0.1 mole) of free amine prepared as above, 10.1 g of triethylamine (0.1 mole) and 100 mL of dichloromethane are taken in a 3-neck round-bottom flask equipped with a condenser and stirring means. The contents of the flask are cooled to 20° C. and 10.45 g of methcryloyl chloride (0.1 mole) is added dropwise with stirring over a period of 60 minutes. The contents are stirred at room temperature for 16 hours. 10 mg of 4-methoxyphenol is added the and the contents are concentrated. To the concentrate is added 250 mL of acetone and the NaCl is filtered. The filtrate is then concentrated under reduced pressure to obtain the 3-(methacrylamidoethyl)-5,5'-dimethyl hydantoin monomer.

Example 2

A polymer is made by polymerizing the monomer of Example 1 as follows. To a 250 mL round-bottom flask fitted with a condenser, stirrer, nitrogen inlet is placed 6.16 g of the product of example 3, 17.5 g of a mixture of water/ethanol (63/37 weight ratio). The contents of the flask are heated with nitrogen sparging and stirring to 62° C. 0.061 g of Vazo™ 56 (Dupont) initiator is added in one shot. Two more initiator shots (0.03 g Vazo 56 initiator) are added after 3 hours and after 5 hours following the first initiator addition. Stirring at 62° C. is continued for 3 more hours and the mixture is cooled to room temperature.

Example 3

A monomer according to the formula:

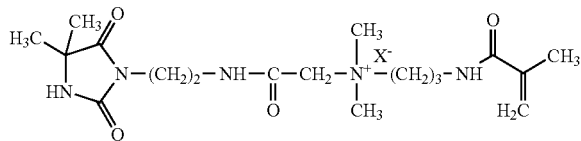

was made as follows. A mixture of dimethylaminopropyl methacrylamide (15.5 g, 0.091 mole), methyl chloroacetate (10.8 g, 0.1 mole), 20 mg of MEHQ and 20 mL of methanol is heated with stirring to 70° C. and are maintained at this temperature for 8 hours and are then cooled to room temperature. 3-(2-aminoethyl)-5,5-dimethyl hydantoin is made as described in Example 1 (17.1 g in 30 mL of methanol) and added over a period of 10 minutes. The contents are then heated to 70° C. with stirring and are maintained at this temperature for 4 hours. The methanol is then distilled under reduced pressure to obtain a viscous product. 41.0 g of water is added to obtain a clear solution.

Example 4

A polymer is made by polymerizing the monomer of Example 3 as follows. To a 250 mL round-bottom flask fitted with a condenser, stirring and a nitrogen inlet is placed a mixture of 20.0 g (50% solution, 0.024 mole) of monomer of Example 3, and water (10.0 g). With nitrogen sparging and stirring the contents of the flask are heated to 62° C. 0.12 g of Vazo 56 initiator in 5.0 mL of water is added over a period of 25 min. After three hours, a second initiator portion (0.04 g Vazo 56 initiator in 2 mL water) is added in one shot. Then after 2 hours, a third initiator portion (0.04 g Vazo 56 initiator in 1 mL water) is added in one shot and the reaction temperature is increased to 68° C. Stirring is continued for 3 hours and the mixture is then cooled to room temperature.

Example 5

A copolymer is made by copolymerizing the monomer of Example 3 with acrylamide as follows. To a 250 mL round-bottom flask fitted with a condenser, stirring and a nitrogen inlet is placed 20.0 g (50% solution in water, 0.024 mole) of monomer from Example 3, 5.37 g of acrylamide (50% solution in water, 0.038 mole) and 10.0 g of water. With nitrogen sparging and stirring the contents of the flask is heated to 62° C. 0.12 g of Vazo 56 initiator in 5.0 mL of water is added over a period of 5 minutes. After 30 minutes, 25 mL of water is added for good stirring. After 4 hours, a second initiator portion (0.04 g Vazo 56 initiator in 2 mL water) is added in one shot. Then after 2 hours a third initiator portion (0.04 g Vazo 56 initiator in 1 mL water) is added in one shot and the reaction temperature is increased to 70° C. Stirring is continued for 3 hours and the mixture is then cooled to room temperature.

The invention claimed is:

1. A monomer according to formula (I):

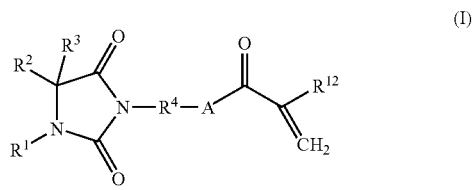

wherein:
R$^1$ is H, chloro, bromo, alkyl, hydroxyalkyl, aryl, or aralkyl,
R$^2$ and R$^3$ are each independently H, alkyl, hydroxyalkyl, aryl, aralkyl, uriedo, or carboxyalkylene,
R$^4$ is,

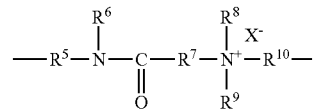

R$^5$, R$^7$, and R$^{10}$ are each independently alkylene,
R$^6$, R$^8$, and R$^9$ are each independently H or alkyl,
A is O or N—R$^{11}$,
R$^{11}$ is H or alkyl,
R$^{12}$ is H or (C$_1$-C$_6$)alkyl, and
X$^-$ is an anion.

2. A monomer according to claim 1, wherein R$_1$ is H, or (C$_1$-C$_6$)alkyl, phenyl, or benzyl.

3. A monomer according to claim 1, wherein R$^2$ and R$^3$ are each independently H, or (C$_1$-C$_6$)alkyl, phenyl or benzyl.

4. A monomer according to claim 1, wherein R$^5$, R$^7$, and R$^{10}$ are each independently (C$_1$-C$_6$)alkylene.

5. A monomer according to claim 1, wherein R$^6$, R$^8$, and R$^9$ are each independently H or (C$_1$-C$_6$)alkyl.

6. A monomer according to claim 1, wherein A is N-R$^{11}$.

7. A monomer according to claim 1, wherein R$^{11}$ is H or (C$_1$-C$_6$)alkyl.

8. A monomer according to claim 1, wherein X is chloro or bromo.

9. A monomer according to claim 1, wherein R$^{12}$ is H or methyl.

10. A monomer of claim 1, wherein:
R$^1$ is H, (C$_1$-C$_{12}$)alkyl, hydroxy(C$_1$-C$_{12}$)alkyl, phenyl, or benzyl,
R$^2$ and R$^3$ are each independently H, (C$_1$-C$_{12}$)alkyl, hydroxy(C$_1$-C$_{12}$)alkyl, phenyl, benzyl, uriedo, or carboxy(C$_1$-C$_{12}$)alkylene,
R$^5$, R$^7$, and R$^{10}$ are each independently (C$_1$-C$_{12}$)alkylene,
R$^6$, R$^8$, and R$^9$ are each independently H or (C$_1$-C$_{12}$)alkyl,
A is O or N-R$^{11}$,
R$^{11}$ is H or (C$_1$-C$_{12}$)alkyl,
X is an anion, and $R^{12}$ is H or $(C_1-C_6)$alkyl.

11. A monomer of claim 1, wherein $R^1$ is H, or $(C_1-C_6)$alkyl, phenyl, or benzyl, $R^2$ and $R^3$ are each independently H, or $(C_1-C_6)$alkyl, phenyl or benzyl, $R^5$, $R^7$, and $R^{10}$ are each independently $(C_1-C_6)$alkylene, $R^6$, $R^8$, and $R^9$ are each independently H or $(C_1-C_6)$alkyl, A is O or N-$R^{11}$, $R^{11}$ is H or $(C_1-C_6)$alkyl, and X is an anion, and, $R^{12}$ is H or $(C_1-C_6)$alkyl.

12. A monomer according to claim 1, wherein $R^1$ is H, methyl, or ethyl, $R^2$ and $R^3$ are each independently H, methyl, or ethyl, $R^5$, $R^7$, and $R^{10}$ are each independently methylene, dimethylene, or trimethylene, $R^6$, $R^8$, and $R^9$ are each independently H, methyl or ethyl, A is N-$R^{11}$, $R^{11}$ is H, methyl or ethyl, X is chloro or bromo, and $R^{12}$ is H or methyl.

13. A monomer according to claim 1, wherein the monomer is according to the formula:

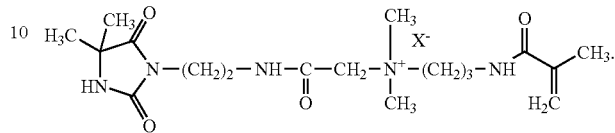

* * * * *